(12) United States Patent
Islam et al.

(10) Patent No.: US 7,372,562 B2
(45) Date of Patent: May 13, 2008

(54) DYNAMIC RANDOM SEPARATION AMONG NANOPARTICLES FOR NANO ENHANCED RAMAN SPECTROSCOPY (NERS) MOLECULAR SENSING

(75) Inventors: M. Saif Islam, Sacramento, CA (US); Shih-Yuan Wang, Palo Alto, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 148 days.

(21) Appl. No.: 11/252,146

(22) Filed: Oct. 17, 2005

(65) Prior Publication Data

US 2007/0086002 A1    Apr. 19, 2007

(51) Int. Cl.
*G01J 3/44* (2006.01)
*G01N 21/90* (2006.01)

(52) U.S. Cl. ............... 356/301; 356/427; 977/786
(58) Field of Classification Search ............ 977/786, 977/787; 356/301, 426, 427, 428
See application file for complete search history.

(56) References Cited

U.S. PATENT DOCUMENTS

| | | | |
|---|---|---|---|
| 4,674,878 A | 6/1987 | Vo-Dinh | |
| 4,944,985 A | 7/1990 | Alexander et al. | |
| 5,017,007 A | 5/1991 | Milne et al. | |
| 5,139,334 A * | 8/1992 | Clarke | 356/301 |
| 5,242,828 A | 9/1993 | Bergstrom et al. | |
| 5,255,067 A | 10/1993 | Carrabba et al. | |
| 5,527,712 A | 6/1996 | Sheehy | |
| 5,609,907 A | 3/1997 | Natan | |
| 5,646,039 A * | 7/1997 | Northrup et al. | 435/287.2 |
| 5,772,905 A | 6/1998 | Chou | |
| 5,837,552 A | 11/1998 | Cotton et al. | |
| 5,885,753 A | 3/1999 | Crooks et al. | |
| 6,025,202 A | 2/2000 | Natan | |
| 6,149,868 A | 11/2000 | Natan et al. | |
| 6,165,911 A | 12/2000 | Calveley | |

(Continued)

FOREIGN PATENT DOCUMENTS

WO    WO 98/10289 A1    3/1998

(Continued)

OTHER PUBLICATIONS

Collier, C.P., et al., "Reversible Tuning of Silver Quantum Dot Monolayers Through the Metal-Insulator Transition," Science, vol. 277, pp. 1978-1981, Sep. 26, 1997.

(Continued)

*Primary Examiner*—Layla G. Lauchman
*Assistant Examiner*—Bryan J Giglio

(57) ABSTRACT

A system for performing nanostructure-enhanced Raman spectroscopy (NERS) includes a radiation source, a radiation detector configured to detect Raman scattered radiation scattered by an analyte, and a container configured to provide a sealed enclosure. The NERS system further includes a turbulence generating device configured to generate random dynamic motion of a plurality of nanoparticles within the container. A method for performing NERS includes providing a container configured to provide a sealed enclosure, providing a plurality of nanoparticles each comprising a NERS-active material and an analyte within the container, causing random dynamic motion of the plurality of nanoparticles and the analyte, irradiating the plurality of nanoparticles and the analyte with radiation, and detecting Raman scattered radiation scattered by the analyte.

24 Claims, 3 Drawing Sheets

U.S. PATENT DOCUMENTS

| | | |
|---|---|---|
| 6,242,264 B1 | 6/2001 | Natan et al. |
| 6,248,674 B1 | 6/2001 | Kamins et al. |
| 6,291,924 B1 | 9/2001 | Lau et al. |
| 6,365,059 B1 | 4/2002 | Pechenik |
| 6,406,777 B1 | 6/2002 | Boss et al. |
| 6,432,740 B1 | 8/2002 | Chen |
| 6,579,721 B1 | 6/2003 | Natan et al. |
| 6,623,977 B1 | 9/2003 | Farquharson et al. |
| 6,649,683 B2 | 11/2003 | Bell |
| 6,773,616 B1 | 8/2004 | Chen et al. |
| 6,808,954 B2 | 10/2004 | Ma et al. |
| 6,861,263 B2 | 3/2005 | Natan |
| 7,008,796 B2* | 3/2006 | Wohlstadter et al. ........ 436/172 |
| 2003/0030800 A1* | 2/2003 | Golden et al. .............. 356/301 |
| 2003/0120137 A1 | 6/2003 | Pawluczyk |
| 2003/0157732 A1 | 8/2003 | Baker et al. |
| 2003/0186240 A1* | 10/2003 | Su et al. ........................ 435/6 |
| 2003/0231304 A1 | 12/2003 | Chan et al. |
| 2004/0077844 A1 | 4/2004 | Jacobson et al. |
| 2004/0126790 A1* | 7/2004 | Su et al. ........................ 435/6 |
| 2004/0135997 A1 | 7/2004 | Chan et al. |
| 2004/0142484 A1* | 7/2004 | Berlin et al. ................ 436/171 |
| 2005/0084980 A1* | 4/2005 | Koo et al. .................. 436/171 |
| 2005/0110990 A1* | 5/2005 | Koo et al. .................. 356/301 |
| 2005/0147979 A1* | 7/2005 | Koo et al. ........................ 435/6 |
| 2005/0264817 A1* | 12/2005 | Havard et al. .............. 356/442 |
| 2006/0028908 A1* | 2/2006 | Suriadi et al. .............. 366/146 |
| 2006/0183236 A1* | 8/2006 | Berlin et al. .................. 436/94 |
| 2006/0240573 A1* | 10/2006 | Kao et al. .................... 436/524 |

FOREIGN PATENT DOCUMENTS

WO     WO 2004/059279 A2     7/2004

OTHER PUBLICATIONS

Garcia-Vidal, F.J., et al., "Collective Theory for Surface Enhanced Raman Scattering," Physical Review Letters, vol. 77, No. 6, pp. 1163-1166, Aug. 5, 1996.

Lu, Yu, et al., "High-Density Silver Nanoparticle Film with Temperature-Controllable Interparticle Spacing for a Tunable Surface Enhanced Raman Scattering Substrate," Nano Lett., vol. 5, No. 1, pp. 5-9, 2005.

Nie, Shuming, et al., "Probing Single Molecules and Single Nanoparticles by Surface-Enhanced Raman Scattering," Science, vol. 275, pp. 1102-1106, Feb. 21, 1997.

Michaels, et al., Surface Enhanced Raman Spectroscopy of Individual Rhodamine 6G Molecules on Large Ag Nanocrystals, J. Am. Chem. Soc., Oct. 14, 1999, 121, pp. 9932-9939.

* cited by examiner

DYNAMIC RANDOM SEPARATION AMONG NANOPARTICLES FOR NANO ENHANCED RAMAN SPECTROSCOPY (NERS) MOLECULAR SENSING

FIELD OF THE INVENTION

The present invention relates to nano-enhanced Raman spectroscopy (NERS). More particularly, the invention relates to systems for performing NERS and to methods for performing NERS using such systems.

BACKGROUND OF THE INVENTION

Raman spectroscopy is a well-known technique for analyzing molecules or materials. In conventional Raman spectroscopy, high intensity monochromatic radiation provided by a radiation source, such as a laser, is directed onto an analyte (or sample) that is to be analyzed. In Raman spectroscopy, the wavelength of the incident radiation typically is varied over a range of wavelengths within or near the visible region of the electromagnetic spectrum. A majority of the photons of the incident radiation are elastically scattered by the analyte. In other words, the scattered photons have the same energy, and thus the same wavelength, as the incident photons. However, a very small fraction of the photons are inelastically scattered by the analyte. Typically, only about 1 in $10^7$ of the incident photons are inelastically scattered by the analyte. These inelastically scattered photons have a different wavelength than the incident photons. This inelastic scattering of photons is termed "Raman scattering". The Raman scattered photons can have wavelengths less than, or, more typically, greater than the wavelength of the incident photons.

When an incident photon collides with the analyte, energy can be transferred from the photon to the molecules or atoms of the analyte, or from the molecules or atoms of the analyte to the photon. When energy is transferred from the incident photon to the analyte, the Raman scattered photon will have a lower energy and a corresponding longer wavelength than the incident photon. These Raman scattered photons having lower energy than the incident photons are collectively referred to in Raman spectroscopy as the "Stokes radiation." A small fraction of the analyte molecules or atoms can be in an energetically excited state when photons are incident thereon. When energy is transferred from the analyte to the incident photon, the Raman scattered photon will have a higher energy and a corresponding shorter wavelength than the incident photon. These Raman scattered photons having higher energy than the incident photons are commonly referred to in Raman spectroscopy as the "anti-Stokes radiation." The Stokes radiation and the anti-Stokes radiation collectively are referred to as the Raman scattered radiation or the Raman signal.

The Raman scattered radiation is detected by a detector that typically includes a wavelength-dispersive spectrometer and a photomultiplier for converting the energy of the impinging photons into an electrical signal. The characteristics of the electrical signal are at least partially a function of both the energy of the Raman scattered photons as evidenced by their wavelength, frequency, or wave number, and the number of the Raman scattered photons as evidenced by the intensity of the Raman scattered radiation. The electrical signal generated by the detector can be used to produce a spectral graph illustrating the intensity of the Raman scattered radiation as a function of the wavelength of the Raman scattered radiation. Analyte molecules and materials generate unique Raman spectral graphs. The unique Raman spectral graph obtained by performing Raman spectroscopy can be used for many purposes including identification of an unknown analyte, or determination of physical and chemical characteristics of a known analyte.

Raman scattering of photons is a weak process. As a result, powerful, costly laser sources typically are used to generate high intensity incident radiation to increase the intensity of the weak Raman scattered radiation for detection. Surface-enhanced Raman spectroscopy (SERS) is a technique that allows for enhancement of the intensity of the Raman scattered radiation relative to conventional Raman spectroscopy. In SERS, the analyte molecules typically are adsorbed onto or placed adjacent to what is often referred to as a SERS-active structure. SERS-active structures typically include a metal surface or structure. Interactions between the analyte and the metal surface may cause an increase in the intensity of the Raman scattered radiation. The mechanism by which the intensity of the Raman scattered radiation is enhanced is not completely understood. Two main theories of enhancement mechanisms have been presented in the literature: electromagnetic enhancement and chemical enhancement. For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932-39 (1999).

Several types of metallic structures have been employed in SERS techniques to enhance the intensity of Raman scattered radiation that is scattered by analyte molecules adjacent thereto. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface made from gold or silver can enhance the Raman scattering intensity by factors of between $10^3$ and $10^6$.

Recently, Raman spectroscopy has been performed employing randomly oriented nanostructures, such as nanometer scale needles, particles, and wires, as opposed to a simple roughened metallic surface. This process will be referred to hereinafter as nano-enhanced Raman spectroscopy (NERS). The intensity of the Raman scattered photons from a molecule adsorbed on such a nanostructure can be increased by factors as high as $10^{16}$. At this level of sensitivity, NERS has been used to detect single molecules. Detecting single molecules with high sensitivity and molecular specificity is of great interest in the fields of chemistry, biology, medicine, pharmacology, and environmental science.

It is unknown what metallic particle configurations, including particle size, particle shape and particle spacing will enhance the intensity of Raman scattered radiation most effectively for any-given analyte. Therefore, the metallic particles used in NERS typically have a variety of sizes and are randomly oriented and positioned to provide a wide range of particle configurations. When such a structure is used to perform NERS, typically only a few small, localized areas of the NERS-active structure provide a configuration that will substantially enhance the Raman scattering of radiation by the analyte molecules disposed in those areas. Other areas of the NERS-active structure do not substantially enhance the intensity of Raman scattered radiation and, therefore, do not contribute to the utility of the NERS-active structure. In addition, if the particle configuration provided by a NERS-active structure does not significantly enhance the intensity of Raman scattered radiation for a given analyte, a new NERS-active structure having a different particle configuration must be provided. Accordingly, there is a need for a NERS-active structure that provides spacing between metallic particles that can be varied or changed to allow for the enhancement of the intensity of Raman scattered radiation scattered by an analyte in the vicinity of the metallic particles.

Hyper-Raman spectroscopy is another Raman spectroscopy technique that involves detecting higher order wavelengths of Raman scattered radiation. An analyte may be excited by more than one incident photon and subsequently relax, emitting a single photon having energy on the order of the combined energy of the incident photons. In this manner, the hyper-Raman scattered radiation may be Raman shifted relative to integer multiples of the wavelength of the incident electromagnetic radiation. Hyper-Raman scattered radiation can provide information about the analyte that cannot be obtained from simple Raman spectroscopy. The intensity of the hyper-Raman scattered radiation, however, is even less than the intensity of the Raman scattered radiation and may be difficult to detect.

BRIEF SUMMARY OF THE INVENTION

The present invention relates to nanostructure-enhanced Raman spectroscopy (NERS). More particularly, the invention relates to systems for performing NERS and to methods for performing NERS using such systems.

In one aspect, the present invention includes a NERS system having a radiation source, a radiation detector configured to detect Raman scattered radiation scattered by an analyte, a container configured to provide a sealed enclosure, and a turbulence generating device configured to generate random dynamic motion of a plurality of nanoparticles within the container.

In another aspect, the present invention includes A NERS system having a radiation source, a radiation detector configured to detect Raman scattered radiation scattered by an analyte, and a container configured to provide a sealed enclosure, a plurality of nanoparticles comprising a NERS-active material disposed within the container. The NERS system further includes means for causing random dynamic motion of the plurality of nanoparticles within the container.

In yet another aspect, the present invention includes a method for performing NERS. The method includes providing a container configured to provide a sealed enclosure, providing a plurality of nanoparticles each comprising a NERS-active material within the container, providing an analyte within the container, causing random dynamic motion of the plurality of nanoparticles and the analyte within the container, irradiating the plurality of nanoparticles and the analyte with radiation, and detecting Raman scattered radiation scattered by the analyte.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention relates to nanostructure-enhanced Raman spectroscopy (NERS). More particularly, the invention relates to systems for performing NERS and to methods for performing NERS using such systems.

The term "NERS-active material" as used herein means a material that, when formed into appropriate geometries or configurations, is capable of increasing the number of Raman scattered photons that are scattered by an analyte when the analyte is located proximate to that material, and the analyte and material are subjected to electromagnetic radiation. NERS-active materials include, but are not limited to, silver, gold, and copper.

The term "nanoparticle" as used herein means a particle of any shape having cross-sectional dimensions of less than about 100 nanometers. Examples of nanoparticles include, but are not limited to, nanodots, nanowires, nanocolumns, and nanospheres.

The term "analyte" as used herein means any molecule, molecules, material, substance, or matter that is to be analyzed by NERS.

The term "turbulence" as used herein means a quality or state of being that is characterized by random dynamic motion.

The illustrations presented herein are not meant to be actual views of any particular NERS system, but are merely idealized representations which are employed to describe the present invention. Additionally, elements common between figures may retain the same numerical designation.

Figure 1:
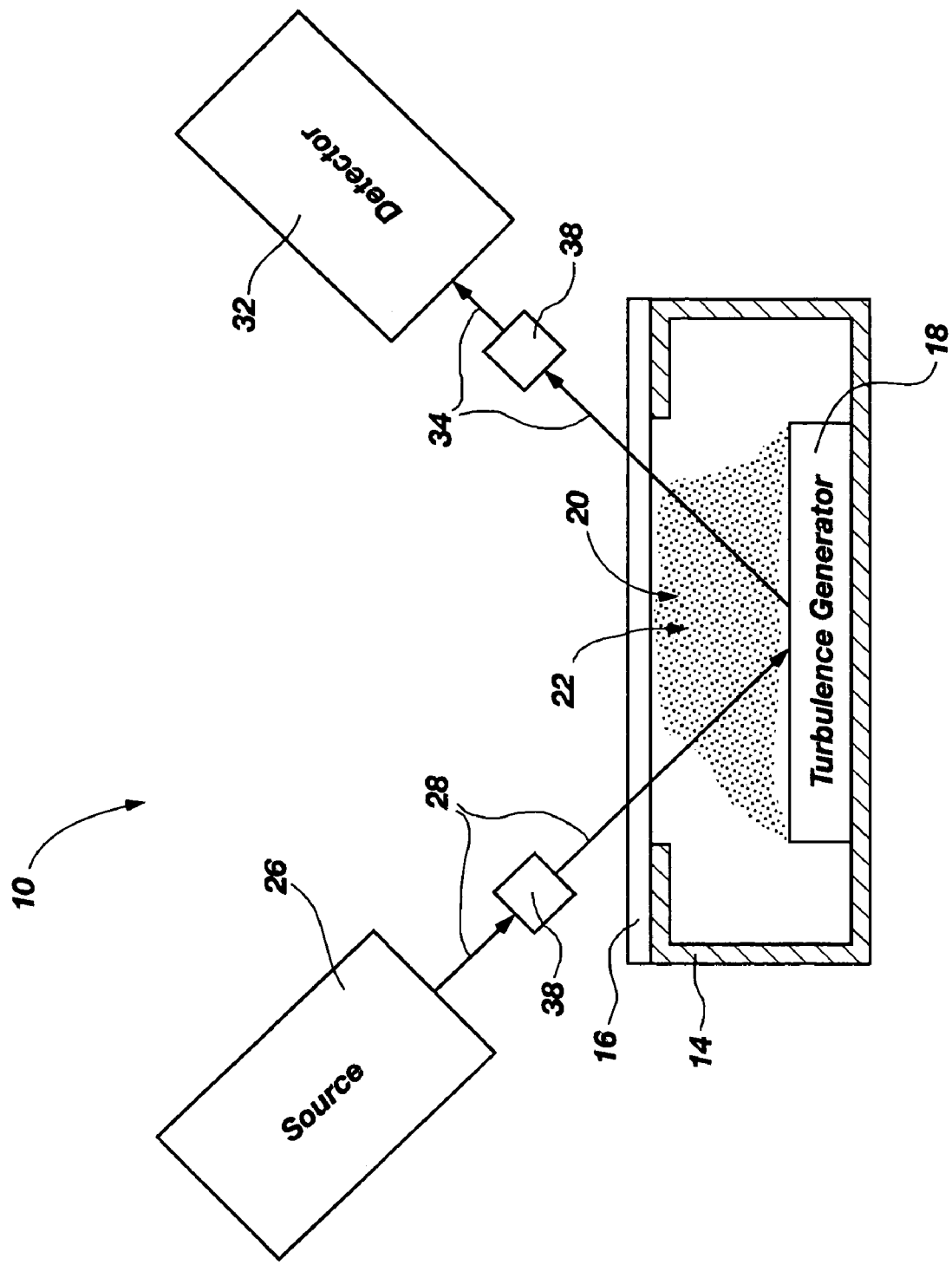
FIG. 1 is a schematic diagram of a representative NERS system that embodies teachings of the present invention.

A representative NERS system 10 that embodies teachings of the present invention and that may be used to perform NERS on an analyte is illustrated schematically in FIG. 1. The NERS system 10 may include a container 14 configured to provide a sealed enclosure, a radiation source 26 for providing incident radiation 28, and a radiation detector 32 for detecting Raman scattered radiation 34. The container 14 may contain a plurality of nanoparticles 20 comprising a NERS-active material and an analyte 22 that is to be analyzed using the NERS system 10. The NERS system 10 also may include various optical components 38 such as, for example, lenses and filters, positioned between the radiation source 26 and the container 14 and between the container 14 and the radiation detector 32.

The NERS system 10 further may include a turbulence generating device 18 configured to generate random dynamic motion of a plurality of nanoparticles 20 within the container 14. Exemplary devices that may be used as the turbulence generating device 18 are described in further detail herein below. The turbulence generating device 18 may be positioned at any location within the container 14.

Alternatively, the turbulence generating device 18 may be disposed outside the container 14 and coupled thereto, or the turbulence generating device 18 may be integrally formed with the container 14. For example, the container 14 itself may be configured as a turbulence generating device. Any configuration that may be used to generate random dynamic motion of a plurality of nanoparticles within the container is acceptable.

At least a portion of the container may be transparent to the incident radiation 28 and to the Raman scattered radiation 34. For example, the container 14 may include a cover 16 that is transparent to the incident radiation 28 and to the Raman scattered radiation 34. The container 14 and the cover 16 may be configured to provide an airtight, hermetically sealed enclosure when it is desired to perform NERS using the NERS system 10.

In this configuration, NERS may be performed while the analyte 22 and the nanoparticles 20 are disposed within the container 14 and the nanoparticles 20 are in a state of random dynamic motion caused by the turbulence generating device 18.

The radiation source 26 may include any device capable of emitting incident radiation 28 at a desired wavelength. Furthermore, the radiation source 26 may be capable of emitting a tunable wavelength of radiation. For example, commercially available semiconductor lasers, helium-neon lasers, carbon dioxide lasers, radiation emitting diodes, incandescent lamps, and many other known radiation emitting devices may be used as the radiation source 26. The wavelengths of the incident radiation 28 that are emitted by the radiation source 26 may be any suitable wavelength for performing NERS on the analyte 22. A representative range of wavelengths that may be emitted by the radiation source 26 includes wavelengths between about 350 nanometers and about 1000 nanometers.

The radiation detector 32 receives and detects the Raman scattered radiation 34 generated by Raman scattered photons that are scattered by the analyte 22. The radiation detector 32 may include a device for determining the wavelength of the Raman scattered radiation 34, such as, for example, a monochromator, and a device for determining the intensity of the Raman scattered radiation 34 such as, for example, a photomultiplier. Typically, the Raman scattered radiation 34 is scattered in all directions relative to the container 14. Thus, the position of the radiation detector 32 relative to the container 14 is not particularly important. However, the radiation detector 32 may be positioned at, for example, an angle of about 90° relative to the direction of the incident radiation 28 to minimize the intensity of any incident radiation 28 that impinges unintentionally on the radiation detector 32.

Optical components 38 positioned between the radiation source 26 and the container 14 may be used to collimate, filter, or focus the incident radiation 28 before the incident radiation 28 impinges on the container 14, the nanoparticles 20, and the analyte 22. Optical components 38 positioned between the container 14 and the detector 32 can be used to collimate, filter, or focus the Raman scattered radiation 34. For example, a filter or a plurality of filters may be employed to prevent radiation at wavelengths corresponding to the incident radiation 28 from impinging on the radiation detector 32, thus allowing only the Raman scattered radiation 34 to be received by the radiation detector 32.

To perform NERS using the NERS system 10, an analyte 22 and a plurality of nanoparticles 20 comprising a NERS-active material may be provided within the container 14 of the NERS system 10. An inert gas optionally may be provided within the container 14. The turbulence generating device 18 may be used to cause random dynamic motion of the plurality of nanoparticles 20 and the analyte 22 within the container 14. The nanoparticles 20 and the analyte 22 may be irradiated with incident radiation 28 provided by the radiation source 26. Raman scattered radiation 34 scattered by the analyte 22 may be detected with the radiation detector 32. As discussed previously herein, the nanoparticles 20 may enhance the intensity of the Raman scattered radiation 34 scattered by the analyte 22 when the nanoparticles are disposed in or provide a certain configuration. As the nanoparticles 20 move about within the container 14 in a random dynamic manner, at any given moment at least two of the nanoparticles 20 may provide a configuration (i.e., size and shape of the nanoparticles 20 and spacing between the nanoparticles 20) that will enhance the intensity of Raman scattered radiation scattered by the analyte 22 when the analyte 22 is disposed proximate to those nanoparticles 20. In this manner, as NERS is performed using the NERS system 10, Raman scattered radiation 34 may be generated at varying locations within the container 14 as the nanoparticles 20 and the analyte 22 move about within the container 14 in a random dynamic manner.

The inter-particle spacing between nanoparticles that will enhance the intensity of Raman scattered radiation may depend on the particular analyte being analyzed. NERS systems that embody teachings of the present invention may be used to analyze a wide variety of analytes since at any given moment since a wide variety distances separating nanoparticles may be provided as the nanoparticles move about within the container 14 in a random dynamic manner. The wavelengths and corresponding intensity of the Raman scattered radiation 34 may be determined and used to identify and provide information about the analyte 22.

It should be understood that the plurality of nanoparticles 20 and the analyte 22 may be irradiated with incident radiation 28 provided by the radiation source 26 while using the turbulence generating device 18 to cause random dynamic motion of the plurality of nanoparticles 20 within the container 14. Alternatively, the turbulence generating device 18 may be used to cause random dynamic motion of the plurality of nanoparticles 20 within the container 14 and the nanoparticles 20 then may be allowed to settle. The plurality of nanoparticles 20 and the analyte 22 may be irradiated with incident radiation 28 provided by the radiation source 26. If the intensity of the Raman scattered radiation 34 is not sufficient, the turbulence generating device 18 again may be used to cause random dynamic motion of the plurality of nanoparticles 20 within the container 14, and the plurality of nanoparticles 20 and the analyte 22 again may be irradiated with incident radiation 28 after the nanoparticles 20 and the analyte 22 have settled. This process may be repeated until the nanoparticles sufficiently enhance the intensity of the Raman scattered radiation 34.

In this manner the turbulence generating device of NERS systems that embody teachings of the present invention may be used to cause random dynamic motion of a plurality of nanoparticles, and thus to vary the distance between the nanoparticles while performing NERS. The ability to vary the distance between nanoparticles is beneficial while performing NERS since the NERS effect is at least partly dependent upon the inter-particle spacing between the nanoparticles and the optimum inter-particle spacing typically is not known.

Figure 2:
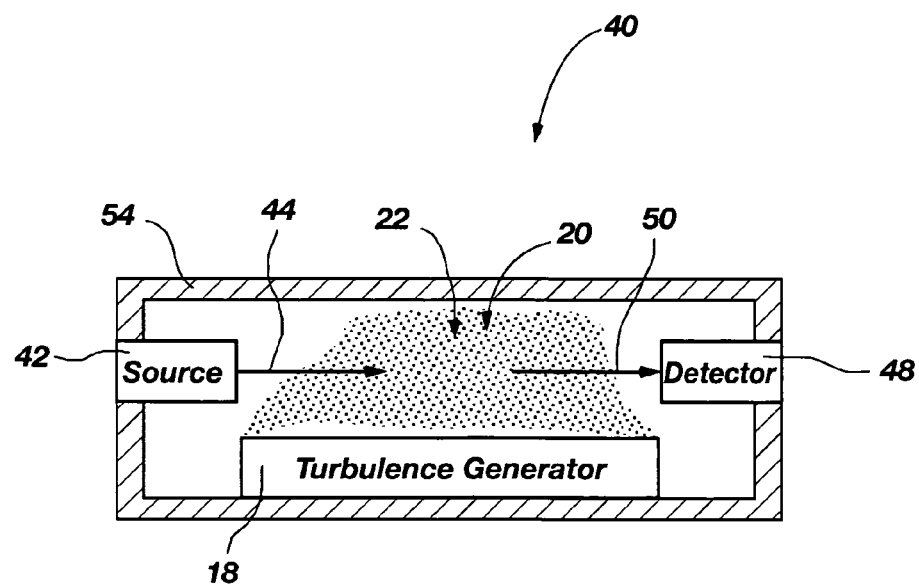
FIG. 2 is a schematic diagram of another representative NERS system that embodies teachings of the present invention.

As seen in FIG. 1, the radiation source 26 and the radiation detector 32 of the NERS system 10 may be disposed outside the container 14. In alternative NERS systems that embody teachings of the present invention, the radiation source, the radiation detector, or both the radiation source and the radiation detector may be disposed within the container. For example, a representative NERS system 40 that embodies teachings of the present invention is shown in FIG. 2. As seen therein, the NERS system 40 may include a radiation source 42 configured to provide incident radiation 44, a radiation detector 48 configured to detect Raman scattered radiation 50 scattered by an analyte 22, a container 54 configured to provide a sealed enclosure, and a turbulence generating device 18 configured to generate random dynamic motion of a plurality of nanoparticles 20 within the container 54. The NERS system 40 also may include various optical components (not shown) similar to the optical components 38 shown in FIG. 1 such as, for example, lenses and filters positioned between the radiation source 42 and the analyte 22 and between the analyte 22 and the radiation detector 32.

The radiation source 42 may include a laser diode. A laser diode may be smaller than many other radiation emitting devices and may facilitate providing the radiation source 42 within the container 54.

In this configuration, the NERS system 40 may be used to perform NERS on an analyte in substantially the same manner as that described previously herein in relation to the NERS system 10 shown in FIG. 1. In particular, a plurality of nanoparticles 20 comprising a NERS-active material may be provided within the container 54 together with an analyte 22. An inert gas optionally may be provided within the container 14. The turbulence generating device 18 then may be used to cause random dynamic motion of the plurality of nanoparticles within the container. The plurality of nanoparticles 20 and the analyte 22 may be irradiated with incident radiation 44 provided by the radiation source 42, and Raman scattered radiation 50 scattered by the analyte 22 may be detected using the radiation detector 48.

Figure 3A:
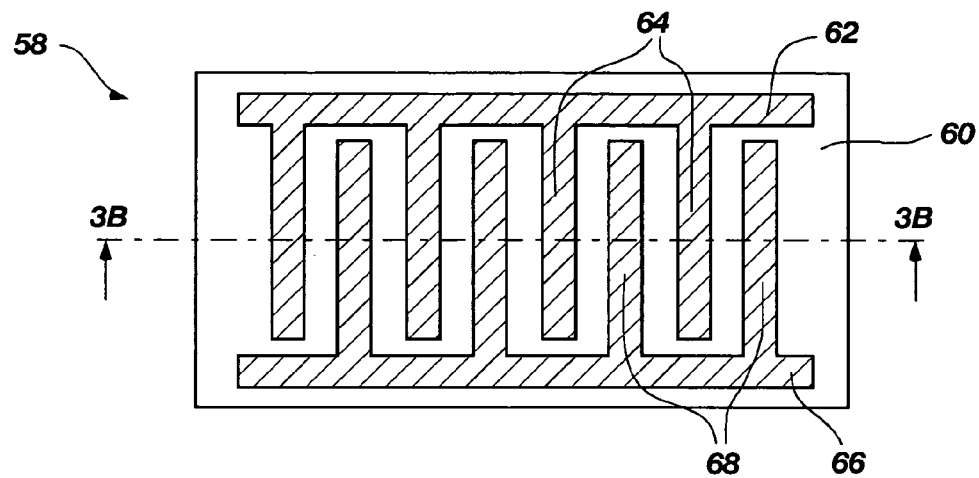
FIG. 3A illustrates a surface acoustic wave device that may be used as a turbulence generating device in the representative NERS systems shown in FIGS. 1-2.
Figure 3B:
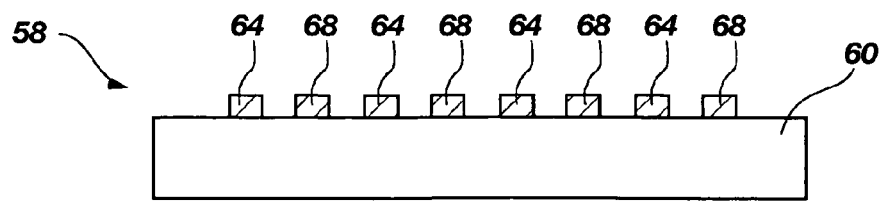
FIG. 3B is a cross-sectional view of the surface acoustic wave device shown in FIG. 3A taken along section line 3B-3B therein.

As described previously herein, NERS systems that embody teachings of the present invention include a turbulence generating device 18 configured to generate or cause random dynamic motion of a plurality of nanoparticles 20. Any device that may be used to cause a plurality of nanoparticles 20 to move in a random dynamic manner may be used as a turbulence generating device 18 in a NERS system embodying teachings of the present invention. Many configurations of known piezoelectric devices may be used as the turbulence generating device 18. For example, a surface acoustic wave (SAW) device may be used as the turbulence generating device 18 shown in FIGS. 1-2. A representative surface acoustic wave device 58 is shown in FIGS. 3A-3B that may be used as the turbulence generating device 18 of the NERS system 10 shown in FIG. 1 and the NERS system 40 shown in FIG. 2. The surface acoustic wave device 58 may include an inter-digital structure disposed on a surface of a substrate 60 and may be configured to convert electrical energy into mechanical energy in the form of elastic mechanical deformation waves in the surface of the substrate 60. These elastic mechanical deformation waves in the surface of the substrate 60 may cause random dynamic motion of a plurality of nanoparticles when the plurality of nanoparticles is disposed on or near the surface acoustic wave device 58.

The surface acoustic wave device 58 may be configured as an inter-digital transducer (IDT). The surface acoustic wave device 58 may include a first sum line 62 and a second sum line 66 that extend generally parallel to one another along a surface of the substrate 60. A first plurality of digits 64 extends laterally from the first sum line 62 towards the second sum line 66. A second plurality of digits 68 extends laterally from the second sum line 66 towards the first sum line 62, the digits of the second plurality of digits 68 being disposed in the spaces between the digits of the first plurality of digits 64.

The substrate 60 of the surface acoustic wave device 58 may be formed from any known piezoelectric material such as, for example, lead zirconate titanate (PZT), barium titanate, or quartz. The first sum line 62, the first plurality of digits 64, the second sum line 66, and the second plurality of digits 68 may be formed from any conductive material including, but not limited to, silver, gold, copper or other metals.

When a voltage is applied between the first plurality of digits 64 and the second plurality of digits 68, the resulting electrical field may induce mechanical deformation in the underlying piezoelectric substrate 60. By applying an alternating voltage between the first plurality of digits 64 and the second plurality of digits 68 a surface acoustic wave may be excited that propagates in a direction substantially perpendicular to the length of the digits of the first plurality of digits 64 and the second plurality of digits 68. An alternating voltage may be applied between the first plurality of digits 64 and the second plurality of digits 68 by, for example, grounding the first sum line 62 and applying an AC electrical signal to the second sum line 66. The wavelength of the generated surface acoustic wave may be at least partially a function of the thickness of the digits of the first plurality of digits 64 and the second plurality of digits 68 and the spacing between the digits of the first plurality of digits 64 and the second plurality of digits 68. The frequency of the generated surface acoustic wave may be at least partially a function of the frequency of the AC electrical signal applied to the second sum line 66.

The surface acoustic wave device 58 may be provided in a container or a NERS system, such as the container 14 of the NERS system 10 shown in FIG. 1, and a plurality of nanoparticles 20 may be provided on or in the vicinity of the surface acoustic wave device 58. An analyte 22 also may be provided within the container 14. The plurality of nanoparticles 20 and the analyte 22 then may be caused to move in a random dynamic manner within the container 14 by supplying electrical energy to the interdigital transducer of the surface acoustic wave device 58 in the form of an electrical signal. The interdigital transducer of the surface acoustic wave device 58 may convert the electrical energy into mechanical energy in the form of surface acoustic waves. These surface acoustic waves may cause the plurality of nanoparticles 20 provided on the surface of the surface acoustic wave device 58 to move in a random dynamic manner. The nanoparticles 20 and the analyte 22 may be irradiated with incident radiation 28 and the Raman scattered radiation 34 scattered by the analyte 22 may be detected as described previously herein.

Figure 4:
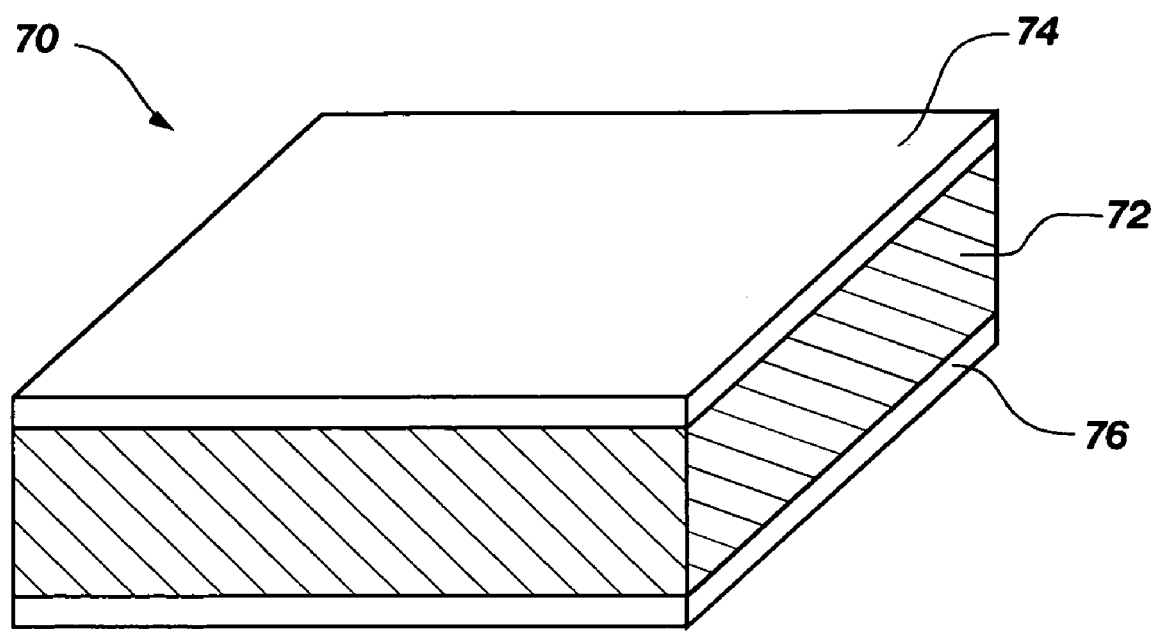
FIG. 4 illustrates a piezoelectric transducer that may be used as a turbulence generating device in the representative NERS systems shown in FIGS. 1-2.

Piezoelectric devices other than surface acoustic wave devices also may be used as a turbulence generating device in NERS systems that embody teachings of the present invention. For example, a simple piezoelectric transducer may be used as the turbulence generating device 18 shown in FIGS. 1-2. A representative piezoelectric transducer 70 is shown in FIG. 4 that may be used as the turbulence generating device 18 of the NERS system 10 shown in FIG. 1 and the NERS system 40 shown in FIG. 2. The piezoelectric transducer 70 may include a piezoelectric material 72, a first electrode 74, and a second electrode 76. The first electrode 74 and the second electrode 76 may be configured such that an electrical voltage may be applied across the piezoelectric material 72 between the first electrode 74 and the second electrode 76. In this configuration, the piezoelectric transducer 70 is configured to convert electrical energy into mechanical energy in the form of mechanical vibrations. These mechanical vibrations may cause random dynamic motion of a plurality of nanoparticles when the plurality of nanoparticles is disposed on or in the vicinity of the piezoelectric transducer 70.

The piezoelectric material 72 of the piezoelectric transducer 70 may be formed from any known piezoelectric material such as, for example, lead zirconate titanate (PZT), barium titanate, or quartz. The first electrode 74 and the second electrode 76 may be formed from any conductive material including, but not limited to, silver, gold, copper or other metals.

A voltage may be applied between the first electrode 74 and the second electrode 76 to generate an electrical field. The electrical field may cause mechanical deformation or distortion of the piezoelectric material 72 between the first electrode 74 and the second electrode 76. For example, the piezoelectric material 72 may be compressed or extended depending on the polarity of the applied voltage and resulting electrical field. By applying an alternating voltage between the first electrode 74 and the second electrode 76, the piezoelectric material 72 may be made to oscillate between extension and compression, thereby producing mechanical vibrations. An alternating voltage may be applied between the first electrode 74 and the second electrode 76 by, for example, grounding the first electrode 74 and applying an AC electrical signal to the second electrode 76. The frequency of the mechanical vibrations may be at least partially a function of the frequency of the AC electrical signal applied to the second electrode 76. Furthermore, the mechanical vibrations may be ultrasonic vibrations.

In this configuration, the piezoelectric transducer 70 may be provided in the container of a NERS system, such as the container 14 of the NERS system 10 shown in FIG. 1, and a plurality of nanoparticles 20 may be provided on a surface of the piezoelectric transducer 70. An analyte 22 also may be provided within the container 14. The plurality of nanoparticles 20 then may be caused to move in a random dynamic manner within the container 14 by supplying electrical energy to the piezoelectric transducer 70 in the form of an electrical signal. The piezoelectric transducer 70 may convert the electrical energy into mechanical energy in the form of mechanical vibrations, which may be ultrasonic vibrations. These mechanical vibrations may cause the plurality of nanoparticles 20 provided on or in the vicinity of the piezoelectric transducer 70 to move in a random dynamic manner. The nanoparticles 20 and the analyte 22 may be irradiated with incident radiation 28 and the Raman scattered radiation 34 scattered by the analyte 22 may be detected as described previously herein.

Furthermore, the plurality of nanoparticles 20 and the analyte 22 may be irradiated with incident radiation 28 while causing random dynamic motion of the plurality of nanoparticles 20 and the analyte 22 within the container 14.

NERS systems that embody teachings of the present invention may include turbulence generating devices other than piezoelectric devices that are configured to generate random dynamic motion of a plurality of nanoparticles. For example, a NERS system may include a turbulence generating device, such as, for example, a fan that is configured to cause an inert gas disposed within a container to flow or move about within the container. Motion of the inert gas within the container may cause random dynamic motion of a plurality of nanoparticles within the container. In this configuration, the fan may be used to generate random dynamic motion of a plurality of nanoparticles within the container.

It should be understood that the NERS system 10 shown in FIG. 1 and the NERS system 40 shown in FIG. 2 also may include a computer device (not shown) configured to control the radiation source, the radiation detector, and the turbulence generating device. The NERS system 10 shown in FIG. 1 and the NERS system 40 shown in FIG. 2 also may include any other required equipment such as electrical cables, circuitry, etc. for providing electrical communication between the computer device and the other components of the NERS system including, but not limited to, the radiation source, the radiation detector, and the turbulence generating device.

The NERS systems and methods disclosed herein allow for improved nanostructure-enhanced Raman spectroscopy techniques and can be employed to enhance the intensity of Raman scattered radiation scattered by an analyte. Moreover, the NERS systems and methods disclosed herein may be used to perform hyper-Raman spectroscopy. The performance of molecular sensors, nanoscale electronics, optoelectronics, and other devices employing the Raman effect may be improved by using the NERS systems and methods disclosed herein.

The NERS systems disclosed herein could be used in spectroscopy techniques other than NERS in which the ability to vary the distance between nanoparticles is beneficial. For example, the NERS systems disclosed herein also might be beneficial for use in emission spectroscopy techniques.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A nano enhanced Raman spectroscory (NERS) system comprising: a radiation source; a radiation detector configured to detect Raman scattered radiation scattered by an analyte; a container configured to provide a sealed enclosure; and a turbulence generating device configured to generate mechanical vibrations causing random dynamic motion of a plurality of nanoparticles each comprising a NERS-active material within the container.

2. A NERS system as recited in claim 1, wherein the container is filled with air or gas and the turbulence generating device comprises a piezoelectrlc transducer supporting the plurality of nanoparticles within the container.

3. A NERS system as recited in claim 1, wherein each nanoparticle of the plurality of nanoparticles comprises one of copper, gold and silver.

4. A NERS system as recited in claim 1, wherein the radiation source is disposed outside the container.

5. A NERS system as recited in claim 1, wherein the radiation source comprises a laser diode disposed within the container.

6. A NERS system as recited in claim 2, wherein the radiation source cormprises a laser diode disposed within the container.

7. A NERS system as recited in claim 1, wherein the turbulence generating device comprises a transducer configured to convert electrical energy into mechanical vibrations.

8. A NERS system as recited in claim 7, wherein the transducer comprises a piezoelectric device.

9. A NERS system as recited in claim 1, wherein the turbulence generating device is configured to generate ultrasonic vibrations.

10. A NERS system as recited in claim 1, wherein the turbulence generating device is configured to generate surface acoustic waves.

11. A NERS system as recited in claim 10, wherein the turbulence generating device comprises a transducer configured to convert electrical energy into surface acoustic waves.

12. A NERS system as recited in claim 11, wherein the transducer comprises a piezoelectric device.

13. A NERS system as recited in claim 1, further comprising an inert gas disposed within the container.

14. A NERS system as recited in claim 13, wherein the turbulence generating device is configured to generate motion of the inert gas within the container, the motion of the inert gas causing random dynamic motion of the plurality of nanoparticles within the container.

15. A nano enhanced Raman spectroscopy (NERS) system comprising: a radiation source; a radiation detector configured to detect Raman scattered radiation scattered by an analyte; a container configured to provide a sealed enclosure; a plurality of nanoparticles comprising a NERS-active material disposed within the container; and means for generating mechanical vibrations and causing random dynamic motion of the plurality of nanoparticles within the container.

16. A NERS system as recited in claim 15, wherein the means for generating mechanical vibrations comprise a piezoelectric transducer.

17. A NERS system as recited in claim 15, wherein the means for generating mechanical vibrations comprise a device configured to generate surface acoustic waves.

18. A method for performing nano enhanced Raman spectroscopy (NERS) comprising: providing a container configured to provide a sealed enclosure; providing a plurality of nanoparticles each comprising a NERS-active material within the container; providing an analyte within the container; generating mechanical vibrations causing random dynamic motion of the plurality of nanoparticles and the analyte within the container; irradiating the plurality of nanoparticles and the analyte with radiation; and detecting Raman scattered radiation scattered by the analyte.

19. A method for performing NERS as recited in claim 18, wherein providing a plurality of nanoparticles each comprising a NERS-active material within the container comprises providing a plurality of nanoparticles each comprising copper, silver, or gold.

20. A method for performing NERS as recited in claim 18, wherein generating mechanical vibrations comprises;
applying an electrical signal to a transducer to generate the mechanical vibrations.

21. A method for performing NERS as recited in claim 20, wherein generating mechanical vibrations comprises generating ultrasonic mechanical vibrations using the transducer.

22. A method for performing NERS as recited in claim 20, wherein generating mechanical vibrations comprises generating surface acoustic waves using the transducer.

23. A method for performing NERS as recited in claim 20, wherein irradiating the plurality of nanoparticles and the analyte with radiation comprises irradiating the plurality of nanoparticles and the analyte with radiation while generating the mechanical vibrations.

24. A method for performing NERS as recited in claim 18, wherein detecting Raman scattered radiation scattered by the analyte comprises detecting hyper-Raman scattered radiation scattered by the analyte.

* * * * *

UNITED STATES PATENT AND TRADEMARK OFFICE
CERTIFICATE OF CORRECTION

| | |
|---|---|
| PATENT NO. | : 7,372,562 B2 |
| APPLICATION NO. | : 11/252146 |
| DATED | : May 13, 2008 |
| INVENTOR(S) | : M. Saif Islam et al. |

It is certified that error appears in the above-identified patent and that said Letters Patent is hereby corrected as shown below:

In column 10, line 48, in Claim 1, delete "spectroscory" and insert -- spectroscopy --, therefor.

In column 10, line 58, in Claim 2, delete "piezoelectrlc" and insert -- piezoelectric --, therefor.

In column 11, line 2, in Claim 6, delete "cormprises" and insert -- comprises --, therefor.

In column 12, line 20, in Claim 20, after "comprises" delete ";".

Signed and Sealed this

Fourteenth Day of July, 2009

JOHN DOLL
*Acting Director of the United States Patent and Trademark Office*